US00PP08424P

United States Patent [19]

Jessel, Jr.

[11] Patent Number: Plant 8,424

[45] Date of Patent: Oct. 19, 1993

[54] CARNATION PLANT NAMED CFPC TYMPANI

[75] Inventor: Walter H. Jessel, Jr., Salinas, Calif.

[73] Assignee: California Florida Plant Co., L.P., Salinas, Calif.

[21] Appl. No.: 976,137

[22] Filed: Nov. 10, 1992

[51] Int. Cl.[5] ..... A01H 5/00

[52] U.S. Cl. ..... Plt./70.1

[58] Field of Search ..... Plt./70.1, 70.2

[56] References Cited

U.S. PATENT DOCUMENTS

P.P. 5,765 7/1986 Nobbio ..... Plt. 70.1

*Primary Examiner*—Howard J. Locker

*Attorney, Agent, or Firm*—Christie, Parker & Hale

[57] ABSTRACT

A new carnation of orange-striped dark pink coloration.

1 Drawing Sheet

SUMMARY OF THE INVENTION

The present invention relates to a new and distinct variety of carnation plant which was originated by me in a controlled breeding program by my crossing as seed parent the variety known as 'Lontarion' (U.S. Plant Pat. No. 5,435), and as pollen parent the variety known as 'Carrier's Fiesta' (U.S. Plant Pat. No. 5,410). The varietal denomination of this new carnation is 'CFPC Tympani'.

Among the novel combination of characteristics possessed by the new variety which distinguishes it from its parents and all other varieties of which I am aware are the attractive flowers of orange-striped dark pink flower coloring of comparatively early flowering response, produced on easily disbudded strong stems, and which exhibit no splitting of the calyx.

Asexual reproduction by propagation by side-shoot cuttings of the new variety as performed in Salinas, Calif. shows that the foregoing and other distinguishing characteristics come true to form and are established and transmitted through succeeding propagations. Although propagation by side-shoot cuttings is described, other known methods of asexual reproduction may also be used to reproduce 'CFPC Tympani'.

Comparison With Closest Variety

The variety believed to be closest to 'CFPC Tympani' is 'Raggio di Sole' (shortened to 'Raggio' herein). The new variety differs from 'Raggio' in a number of characteristics, including flowering response, which is five to six weeks earlier than 'Raggio'. Obviously, the substantial difference in flowering response is extremely important for a cut-flower variety.

BRIEF DESCRIPTION OF THE ILLUSTRATION

The accompanying illustration show a typical specimen of the flower of the new variety depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.). The terminology used in the color descriptions herein refers to plate numbers in the aforementioned color chart. Color descriptions and color descriptions may deviate from the stated values depending upon varying light, environmental, seasonal and cultural conditions.

The information provided herein is based on observations of plants grown inside a commercial greenhouse at Salinas, Calif. in the winter season. The height of plant and flower and foliage size are established as an average using standard commercial cultural practices.

Name: 'CFPC Tympani'.

Classification:

*Botanical.*—*Dianthus caryophyllus.*

*Commercial.*—Carnation, standard disbud type.

Parentage:

*Female parent.*—'Lontarion'.

*Male parent.*—'Carrier's Fiesta'.

Plant:

*Height.*—About 39–42 inches.

*Growing habit.*—Herbaceous, upright.

*Blooming habit.*—Standard, disbud type.

*Blooming season.*—Year-round.

*Rooting time.*—About 16–17 days.

*Mutation prone.*—Does not appear to be.

*Disease resistance.*—Unknown.

*Breaking action.*—Very good.

Foliage:

*Color.*—Upper side: Near to 189A. Lower side: Near to 189A.

*Size.*—About 6¾ inches long; about ⅜ inches wide.

*Quantity.*—Numerous.

*Shape.*—Lanceolate.

*Texture.*—Smooth.

*Ribs.*—Central, keeled.

*Arrangement.*—Bilateral along stem.

*Stem.*—Green.

Bud:

*Shape.*—Oval.

*Color.*—Green.

*Length.*—About 1 inch.

*Diameter.*—About ½ to ⅝ inch.

Calyx:

*Number of sepals.*—About 5.

*Length.*—About 1½ inches.

*Width.*—About ½ inch.

*Color.*—Outside — near to 147C. Inside — near to 150C.

Bloom:

*Shape.*—Round.

*Size.*—Diameter average: About $3\frac{1}{2}$ to $3\frac{3}{4}$ inches. Depth average: About $1\frac{1}{4}$ inches.

*Borne.*—Terminal disbudded as a standard.

*Color.*—General tonality: Orange-striped dark pink. Upper side: Near 32D to 29C with dark pink stripes near 51A to 51B. Lower side: Near to 29C with dark pink stripes near 51A to 51B. Center: Near to 32D. Outer petals: Near 32D to 29C with dark pink, stripes near 51A to 51B.

*Keeping quality.*—Very good, 12–14 days.

*Fragance.*—Slight.

Petals:

*Number.*—About 72.

*Outer petals.*—Length: About 2 inches. Width: About $1\frac{3}{4}$ inches.

*Central petals.*—Length: About 1 inch. Width: About $\frac{1}{3}$ inch.

*Texture.*—Smooth.

*Form.*—Fan-shaped.

*Appearance.*—Shiny.

Reproductive organs (Not visible in this variety):

*Stamens.*—Number: About 5. Arrangement: Around the ovary.

*Anthers.*—Number: About 5. Length: About 1/9 inch. Color: Near to 159A.

*Filaments.*—Length: About 1 inch. Color: Near to 157D.

*Pistil.*—Number: About 4. Color: Style — near 155D. Length: About 1 inch at maturity.

*Stigma.*—Number: About 3. Color: Near 157B.

*Ovary.*—Shape: Conical, ribbed. Color: Base — greenish white. Body — greenish yellow. Apex — tan.

*Fertility.*—Male: Poor. Female: unknown.

I claim:

1. A new and distinct variety of carnation plant, substantially as shown and described.

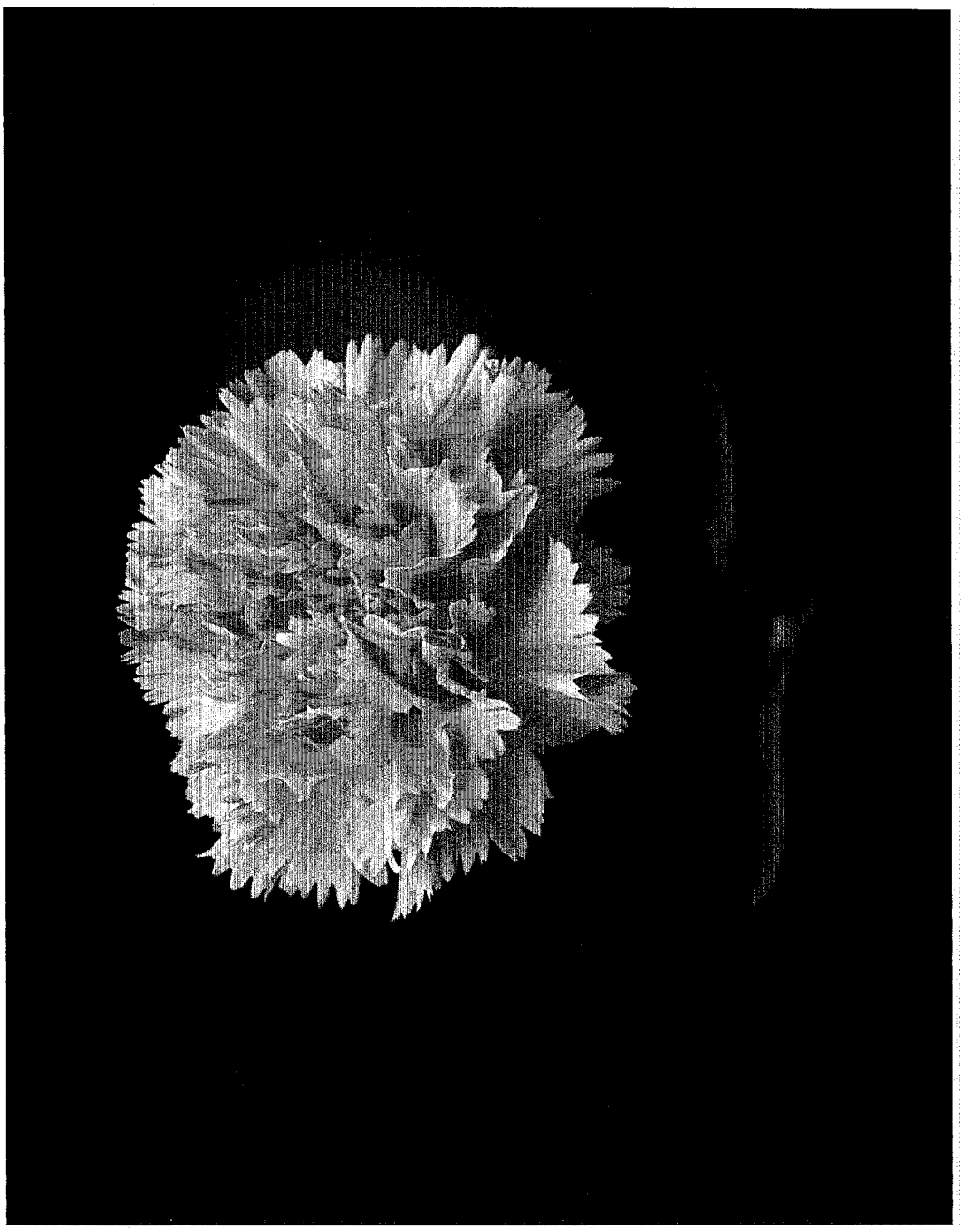

* * * * *